United States Patent [19]

Hammershaimb et al.

[11] Patent Number: 4,835,331

[45] Date of Patent: May 30, 1989

[54] PROCESS FOR THE OLIGOMERIZATION OF OLEFINIC HYDROCARBONS

[75] Inventors: Harold U. Hammershaimb, Western Springs; Robert R. Frame, Glenview, both of Ill.

[73] Assignee: UOP, Des Plaines, Ill.

[21] Appl. No.: 197,370

[22] Filed: May 23, 1988

[51] Int. Cl.[4] ................................................ C07C 2/30
[52] U.S. Cl. ................................... 585/520; 585/521; 585/522; 585/531; 585/532
[58] Field of Search .............. 585/520, 521, 522, 531, 585/532

[56] References Cited

U.S. PATENT DOCUMENTS

| | | | |
|---|---|---|---|
| 3,051,690 | 8/1962 | Vandenburg | 260/88.2 |
| 3,155,642 | 11/1964 | Duck et al. | 260/94.3 |
| 3,170,904 | 2/1965 | Ueda et al. | 260/94.3 |
| 3,170,906 | 2/1965 | Ueda et al. | 260/94.3 |
| 3,457,321 | 7/1969 | Hambling et al. | 260/683.15 |
| 3,483,268 | 12/1969 | Hambling et al. | 260/683.15 |
| 3,483,269 | 12/1969 | Magoon et al. | 260/683.15 |
| 3,505,425 | 4/1970 | Jones et al. | 260/683.15 |
| 3,535,297 | 10/1970 | Carrick et al. | 260/85.3 |
| 3,562,351 | 2/1971 | Mertzweiller et al. | 260/683.15 |
| 3,592,869 | 7/1971 | Cannell | 260/683.15 |
| 3,644,564 | 2/1972 | van Zwet et al. | 260/686.15 |
| 3,663,451 | 5/1972 | Hill | 252/431 R |
| 3,679,772 | 7/1972 | Yoo | 260/680 B |
| 3,697,617 | 10/1972 | Yoo et al. | 260/683.15 |
| 3,755,490 | 8/1973 | Yoo et al. | 260/683.15 |
| 3,954,668 | 5/1976 | Yoo et al. | 252/431 P |
| 4,101,600 | 7/1978 | Zhukov et al. | 260/683.15 |
| 4,232,140 | 11/1980 | Ort | 526/129 |
| 4,357,448 | 11/1982 | Tsubaki et al. | 526/65 |
| 4,383,939 | 5/1983 | Johnstone . | |
| 4,414,369 | 11/1983 | Kuroda et al. | 526/65 |
| 4,423,267 | 12/1983 | Dowling et al. | 585/526 |
| 4,484,016 | 11/1984 | Maschmeyer et al. | 585/522 |
| 4,665,139 | 5/1987 | Veazey et al. | 526/86 |
| 4,665,140 | 5/1987 | Pennington et al. | 526/86 |
| 4,740,652 | 4/1988 | Frame | 585/531 |

FOREIGN PATENT DOCUMENTS 1123474 8/1968 United Kingdom .
1390530 4/1975 United Kingdom .

*Primary Examiner*—H. M. S. Sneed
*Assistant Examiner*—Chung K. Pak
*Attorney, Agent, or Firm*—Thomas K. McBride; Raymond H. Nelson

[57] ABSTRACT

Olefinic feedstocks which contain catalyst contaminants or poisons such as sulfur containing compounds may be oligomerized to a desired product by effecting the reaction in the presence of an added amount of hydrogen to the feedstock. The catalyst which is employed to effect this oligomerization will remain stable and will not deactivate due to the presence of the aforementioned poisons. The catalyst composite will comprise a porous support which has been impregnated with a catalytically effective amount of an iron group metal compound and, if so desired, a compound containing a metal of the Group IVA of the Periodic Table. In addition, the catalyst composite will also contain in combination therewith, a catalytically effective amount of an alkyl aluminum compound and, if so desired, an aluminum alkoxy or aluminum halide compound.

22 Claims, No Drawings

PROCESS FOR THE OLIGOMERIZATION OF OLEFINIC HYDROCARBONS

BACKGROUND OF THE INVENTION

The oligomerization of olefins is known in the art, subh oligomerization processes being effected by treating olefinic hydrocarbons with certain catalysts to obtain various oligomers which will find a useful function in the chemical art. One type of catalyst which may be employed for this particular type of reaction comprises a supported metal compound. For example, U.S. Pat. No. 3,562,351 discloses a method for dimerizing olefins utilizing a supported catalyst which has been prepared by impregnating a suitable support with a salt solution of a Group VIII metal followed by a heat treatment in an inert atmosphere at a temperature less than that which is required to form a metal oxide but which will form a complex on the surface of the solid support. Following this, the catalyst is activated by treatment with an organometallic compound. U.S. Pat. No. 3,483,269 describes a catalyst useful for oligomerizing lower olefins which comprises a $\pi$-allkyl nickel halide supported on an acidic inorganic oxide support. If so desired, the support may have been optionally treated with an alkyl aluminum compound. U.S. Pat. No. 3,592,869 also describes a catalyst which is useful for the oligomerization of olefins. A divalent nickel compound and an alkyl aluminum compound are contacted with an olefinic compound. The resulting mixture is then used to impregnate an inorganic refractory oxide support. Another patent, namely U.S. Pat. No. 3,644,564, describes a catalyst for the oligomerization of ethylene which comprises an organo aluminum-free reaction product of a nickel compound which is an atom of nickel in complex with an olefinically unsaturated compound and a fluorine-containing ligand. The catalysts are typically formed in situ. U.S. Pat. No. 3,679,772 describes a process for reacting monoolefins with diolefins, the catalyst for such a reaction comprising a complex of (1) nickel, (2) a group VA electron donor ligand such as an organophosphine, (3) a nonprotonic Lewis acid and (4) a reducing agent which itself may be a Lewis acid, all of which are composited on an acidic silicabased support.

U.S. Pat. No. 3,697,617 describes an oligomerization process involving the use of a catalyst comprising a complex of nickel with a chloro-containing electron donor ligand such as chlorodiphenylphosphine combined with a nonprotonic Lewis acid which is capable of forming a coordination bond with nickel and a reducing agent capable of reducing nickel acetylacetonate to an oxidation state less than 2. This complex may be composited on a solid support comprising an acidic silica-based material such as silica-alumina. The Lewis acid and the reducing agent may comprise the same compound as, for example, ethyl aluminum sesquichloride. U.S. Pat. No. 3,663,451 describes a catalyst which is obtained by reacting a transition metal halide such as nickel halide with a carrier to give a carrier-metal bond. This product is then reacted with a ligand such as a phosphine or ketone and finally activated by treatment with an aluminum alkyl or chloro alkyl.

U.S. Pat. No. 3,755,490 describes the polymerization of an olefin utilizing a catalyst comprising nickel, a Group VA electron donor ligand, a Lewis acid, and a reducing agent on a solid acidic silica-based support. U.S. Pat. No. 3,954,668 is drawn to an oligomerization catalyst comprising a nickel compound, a chloro-containing electron donor ligand, or a phosphorous compound, a nonprotonic Lewis acid reducing agent which is capable of reducing nickel acetylacetonate to an oxidation state of less than 2 and which is also capable of forming a coordination bond with a nickel. U.S. Pat. No. 3,170,904 speaks to a catalyst which is useful for polymerization comprising a large surface area metal of Groups VIIA or VIII of the Periodic Table, boron trifluoride etherate, an organometallic compound of Groups I, II, III or IV or a halo derivatie ov an organomettallic compound of Groups II, III or IV or a hydride of a metal of Groups I, II or III. The large surface area metal which comprises one component of this catalyst is in metallic form as, for example, Raney nickel. If so desired, the catalyst may be composited on a distomaceous earth carrier. In like manner, U.S. Pat. No. 3,170,906 discloses a catalyst which comprises (A) a carrier-supported nickel or cobalt oxide which has been prepared by impregnating the carrier with the hydroxide, organic acid salt, inorganic acid salt, followed by oxidation in the presence of oxygen or a combination of nitrogen and oxygen; (B) a boron, titanium, zirconium, or vanadium halide; and (C) an alkyl metal or alkyl metal halide. In addition to these patents, British Pat. No. 1,390,530 describes an oligomerization catalyst which has been prepared by thermally pretreating a metal oxide carrier material followed by reacting with a halogen-containing organo-aluminum compound and thereafter in a step-wise fashion, impregnating this product with a divalent nickel or cobalt complex at temperatures ranging from $-50°$ to $150°$ C.

Several other patents which describe oligomerization or polymerization catalysts which are unsupported in nature or processes include Japanese Patent 5024282 which is drawn to a catalyst containing a Group VII metal and tin chloride or zinc chloride as well as Japanese Patent 4722206 which describes an unsupported catalyst prepared by mixing a nickel compound, an aluminum organic compound and a tin tetrahalide. U.S. Pat. No. 3,155,642 describes an unsupported catalyst prepared from an alklyl tin compound and aluminum chloride in addition to a nickel or cobalt compound for the polymerization of a dienic compound. U.S. Pat. No. 3,155,642 also describes an unsupported catalyst comprising a nickel carboxylate, a halide of a metal of Group IV or V and an organoaluminum compound containing at least one alkoxy radical, said catalyst being used for the polymerization of cis-1,4-polybutadiene. Likewise, U.S. Pat. No. 3,457,321 describes an unsupported catalyst prepared from a complex organic compound of a metal of Group VIII, a reducing agent and a tin tetraalkyl compound. Futhermore, U.S. Pat. Nos. 3,483,268 and 3,505,425 are also drawn to unsupported catalysts, the former showing a catalyst comprising nickel acetyl acetonate, an organonickel compound,a nd an activating agent of an aluminum alkyl alkoxide or aluminum trialkyl while the latter is drawn to a process for preparing this catalyst. British Pat. No. 1,123,474 likewise teaches a process for preparing linear dimers using a catalyst comprising a complex organic compound of a metal of a Group VIII and a tin tetraalkyl compound.

In addition to the above patents, other patents have been noted in which a polymerization reaction is effected in the presence of hydrogen. For example, U.S. Pat. Nos. 4,665,139 and 4,665,140 describe a catalyst which is useful for the production of polyethylene having a relatively narrow range of molecular weights. The catalyst which is employed for this reaction comprises an inorganic oxide having surface hydroxyl groups as a support for a vanadium salt and an aluminum alkyl. The hydrogen which is present in the reaction zone or in the ethylene feed is there for the purpose of controlling the molecular weight of the desired polymer and specifically, the higher the ratio of hydrogen to ethylene, the lower the molecular weight. U.S. Pat. No. 4,414,369 describes a process for the preparation of polyethylene in two stages. The catalyst which is utilized to effect this process comprises a transition metal salt such as titanium and magnesium salts supported on a solid carrier. The process involves feeding ethylene to this first stage of said process and an ethylene/hydrogen feed to the second stage. Again, the hydrogen is present to form relatively low molecular weight polymers in the second stage inasmuch as the polymer which is found in the first stage has a relatively high molecular weight. Thus, the product resulting from the two-stage operation contains a polymer having a relatively wide distribution of molecular weights.

U.S. Pat. No. 3,051,690 describes a process for polymerizing olefins in which a hydrogen is utilized as a molecular weigth control agent. The patentee states that he has found that the molecular weight of the polymeric product which is indicated by the viscosity of the product may be controlled within a desired range by the addition of hydrogen to the polymerization system. However, the catalyst which is employed to effect this polymerization comprises a transition metal compound and particularly metal halides such as titanium tetrachloride. The transition metal compound comprises one component comprises an organometallic compound. However, the two-compound catalyst system is not composited on a solid support.

In U.S. Pat. No. 4,383,939, the catalyst which is utilized for the polymerization reaction is prepared by reacting a refractory oxide support with a halogen containing transition metal such as titanium chloride followed by reaction with an alkyl aluminum compound and a transition metal compound of vanadium. The polymerization of olefins is effected in the presence of hydrogen, the purpose of the hydrogen being to control the melt index and thus inversely control the molecular weight of the desired polymeric product. In U.S. Pat. No. 4,357,448, ethylene is polymerized in two steps under different hydrogen partial pressures. However, the catalytic composite which is used to effect this reaction comprises an organoaluminum compound in combination with a catalytic component which has been obtained by reacting a titanium or vanadium halogen-containing compound with the reaction product obtained by reacting a Grignard reagent with a hydropolysiloxane. Again the hydrogen is present to control the molecular weight by controlling the melt index of the product. In U.S. Pat. No. 4,232,140, a feedstock comprising ethylene or ethylene and propylene mixtures is polymerized in the presence of a catalyst comprising triethylene aluminum and a vanadium compound supported on silica gel. The reaction is effected in the presence of hydrogen which again controls the molecular weight properties of the product.

Other patents which relate to polymerization will include U.S. Pat. No. 3,535,297 which discloses a polymerization of ethylene in the presence of a catalyst comprising chromium composited on silica. Again, the use of hydrogen in the reaction mixture is for the purpose of controlling the melt index of the product. U.S. Pat. No. 4,101,600 relates to the dimerization of ethylene in the presence of a two-component catalyst comprising a mixture of an organotitanium and an organoaluminum compound which is not supported. The patent speaks to the use of hydrogen for the purpose of forming low molecular weight products from the titanium catalyst.

It is to be noted from the discussion of the patents in the preceding portion of this specification that the catalysts are for the main part unsupported when used in dimerization or polymerization reaction and utilizes as the active component for the desired reaction a metal such as that of IVB, VB, or VIB of the Periodic Table. This is in contradistinction to the supported catalyst of the present invention which utilizes, as the active metal component thereof, a metal of the iron group of the Periodic Table and, if so desired, a metal of Group IVA of the Periodic Table.

As will hereinafter be shown in greater detail the oligomerization of olefinic hydrocarbons to provide products which possess a desired configuration with respect to the branching or minimal branching of the resultant chain may be accomplished by treating said olefins in the presence of certain catalytic compositions of matter which have been prepared according to the method subsequently described in greater detail, the reaction being effected in the presence of hydrogen which will enable the catalyst to maintain its activity and stability for a relatively long period of time in the presence of certain impurities or poisons which may be inherently present in the olefinic hydrocarbon feedstock.

BRIEF SUMMARY OF THE INVENTION

This invention relates to a process for the oligomerization of olefinic hydrocarbons and more specifically, to an oligomerization process which is effected in the presence of hydrogen and certain catalytic compositions of matter to obtain selective oligomers of the olefinic feedstock.

The term "polymerization" has a relatively broad meaning in the chemical art. Although it is generally referred to as the preparation of relatively high molecular weight polymers, that is, polymers possessing molecular weight of greater than 50,000 or more, it may also refer to low molecular weight polymers, that is, polymers possessing molecular wieghts lower than 50,000. In contradistinction to this, the term "oligomerization" refers to polymeric compounds in which the molecules consist of only a relatively few monomeric units and thus would include dimerization, trimerization or tetramerization.

Many olefinic hydrocarbons which contain from 4 to about 12 carbon atoms in the chain are utilized in various industries in many ways. For example, dimers of propylene, regardless of the amount of branching, may be used to improve the octane number of motor fuels which are utilized in internal combustion engines utilizing gasoline as the fuel thereof. The presence of these compounds in a motor fuel such as gasoline will improve the octane number of the fuel to a high level, thus enabling the gasoline to be utilized in combustion engines in an unleaded state. Other uses for dimers containing 6 carbon atoms would be in the synthesis of flavors, perfumes, medicines, dyes and resins. Another use of an oligomer would be found in the dimerization product of butene in which the dimer which possesses a relatively straight chain configuration with a minimum of branching such as one methyl substituent on the chain would be as an intermediate in the production of a plasticizer. The plasticizer, when added to a plastic, will facilitate compounding and improve the flexibility as well as other properties of the finished product. Likewise, a trimer of butene or a dimer of hexene in which the olefin contains 12 carbon atoms may be used as an intermediate in various organic syntheses such as in the preparation of detergents, lubricants, additives, plasticizers, flavors, perfumes, medicines, oil, dyes, etc. In addition, linearized oligomers containing 12 or more carbon atoms, upo hydrogenation, provide excellent diesel fuels.

It is therefore an object of this invention to provide a process for the oligomerization of olefinic hydrocarbons.

A further object of this invention is to provide a process for the oligomerization of olefinic hydrocarbons which contain inpurities capable of having a deleterious affect upon the catalyst which is employed to effect polymerization reaction.

In one aspect, an embodiment of this invention is found in a process for the oligomerization of an olefinic hydrocarbon which comprises passing a feedstream of an olefinic hydrocarbon into an oligomerization zone, contacting said olefinic hydrocarbon in said oligomerization zone with a catalytic composite which has been prepared by the process of impregnating a porous support with an aqueous solution of an iron group metal salt, calcining said impregnated support at a temperature in the range of from about 300° to about 450° C. and contacting said impregnated calcined support with a solution of an alkyl aluminum compound at oligomerization conditions in the presence of hydrogen to form an oligomer of said olefinic hydrocarbon, and recovering said oligomer.

A specific embodiment of this invention is found in a process for hte oligomerization of propylene which comprises passing a feedstream of said propylene and hydrogen into an oligomerization zone, said hydrogen being present in said feedstream in an amount in the range of from about 0.1 to about 1.0 mole percent, contacting said propylene and hydrogen in said oligomerization zone with a catalytic composite which has been prepared by impregnating alumina with an aqueous solution of a nickel salt and an aqueous solution of a tin salt, calcining said impregnated support at a temperature in the range of from about 300° to about 450° C. and thereafter contacting said impregnated calcined support with a solution containing dimethylaluminum chloride, and aluminum chloride, said contact of said propylene and hydrogen with said catalytic composite being effected at a temperature in the range of from about −20° to about 200° C. and a pressure in the range of from about 2,413 kPa (350 psig) to about 6,895 kPa (1,000 psig) to form an oligomer of said propylene, and recovering said olibomer which comprises a mixture of hexene, methylpentene and dimethylbutene.

DETAILED DESCRIPTION OF THE INVENTION

As hereinbefore set forth, the present invention is concerned with a process for the oligomerization of an olefinic hydrocarbon. The process involves the use of hydrogen as a component of the feedstream which is contacted with a catalytic composite of the type hereinafter described in greater detail. Heretofore, the preparation or oligomerization of olefinic hydrocarbons was relatively difficult to effect inasmuch as several relatively expensive compounds were required for use as components of the composite as well as the entailment of somewhat complicated methods for the manufacture of the composite. In contradistinction to these drawbacks with which prior catalysts are involved, the catalytic composite of the present invention is relatively easy to prepare and, in addition, employs compounds which are less expensive than the components of the other catalysts. The final catalytic composite which is utilized in the process of the present invention would possess a high activity and will be stable over a relatively long period of time.

The olefinic hydrocarbons which are utilized as the feedstock for the process of the oligomerization may contain certain impurities which act to deactivate the catalyst. These impurities may include various sulfur compounds such as carbonyl sulfide, hydrogen sulfides; mercaptans such as methyl mercaptan, ethyl mercaptan, propyl mercaptan, etc.; disulfides such as dimethyl disulfide, diethyl sulfide, etc. In addition, other catalyst deactivating impurities such as oxygenates comprising oxygen-containg organic compounds such as alcohols, including methyl alcohol, ethyl alcohol, propyl alcohol, etc.; ethers such as dimethyl ether, diethyl ether, methyl ethyl ether, methyl propyl ether, etc.; aldehydes such as formaldehyde, acetaldehyde; and ketones such as acetone, methyl ethyl ketone, etc. Generally speaking, the impurities may be present in trace amounts such as in a range of from about 0.1 to about 100 ppm of feedstock. However, even these trace amounts of impurities will have a deleterious effect upon the activity and stability of the oligomerization catalysts and thus quickly deactivate the catalyst when these impurities are present.

As an example of the type of impurities which may be present, feedstocks comprising gases such as ethylene, propylene, butene, etc. which are products from a catalytic cracking process will in some instances be subjected to an extrative sweetening process which largely will remove sulfur which is present in the orignial charge stock to the cracking unit and which will come through and remain with the products from the cracking operation. However, in many instances, the extrative sweetening process is unable to totally remove all of the sulfur and therefore some sulfur compounds will remain in the gas. A particular species which may be expected to remain in these gaseous products comprise dimethyldisulfide.

It has been found that the dimethyldisulfide which is present in the feed mixture which is to undergo oligomerization acts as a contaminant and will posion or deactivate the particular catalytic composite which is used in the process of the present invention.

As was previously discussed, prior patents have utilized hydrogen, in some instances, as a portion of the feedstock for polymerizing reactions to control the molecular weight of the polymer product by controlling the melt index. However, the polymers which are admixed in these patents possess molecular weights which are measured in the hundreds of thousand. Thus, by increasing the melt index of the polymers, which is inverse to the molecular weight, it is possible to obtain polymers which possess a molecular weight within a desired range. In constradistinction to these prior patents, we have now unexpectedly discovered that by employing hydrogen in the present process which involves an oligomerization reaction which results in products comprising a dimer, timer or tetramer of the original olefinic monomer, it is possible to effect the reaction in the presence of contaminants which, under ordinary circumstances, and in the absence of hydrogen, will poison or deactivate the catalyst and thus render the process uneconomical to operate. Furthermore, in contradistinction to the teachings set forth in the prior patents, it has been discovered that the hydrogen present in the reaction zone and as a portion of the olefinic hydrocarbon feed does not affect the molecular weight of the product. For example, over a given set of conditions, hydrogen will increase the conversion of the olefinic hydrocarbon, thus activating the system and will result in the obtention of a greater amount of trimer product rather than dimer product, thus contradicting the teachings of the prior art which allege that the presence of hydrogen will decrease the molecular weight of the product.

The oligomerization process of the present invention which comprises subjecting an olefinic hydrocarbon in the presence of hydrogen to contact with a catalyst more specifically described in a later portion of the specification will result in the conversion of the olefinic hydrocarbons to desired products comprising dimers and trimers of the olefinic monomer. The dimer products produced by the oligomerization of propylene on the n-butenes will possess a percentage of linear compounds, that is, n-hexenes and n-octenes as well as a dimer which contains only one methyl substituent, the more highly branched oligomers being minority products. The propylene dimers which are produced according to the process of the present invention will all possess relatively high octane numbers regardless of the branching, and thus will be utilized as excellent octant blending components. In addition, the n-butene dimers are excellent as intermediates in the preparation of plasticizers. By effecting the oligomerization reaction in the presence of the added hydrogen, it is possible to effect the process for a long period of time, the catalyst maintaining a desired activity as well as stability even in the presence of unwanted impurities.

The catalyst composite of the present invention will comprise a combination of a catalytically effective amount of an alkyl aluminum compound composited on a porous support containing an iron group metal salt. In the preferred embodiment of the invention the iron group metal compound will be obtained from a soluble salt of nickel or cobalt such as, for example, nickel nitrate, nickel hydroxide, nickel bromide, nickel chloride, nickel fluoride, nickel acetate, cobaltic chloride, cobaltous acetate, cobaltous ammonium chloride, cobaltous bromide, cobaltous fluoride, cobaltous perchlorate, cobaltous sulfate, etc.

Examples of alkyl aluminum compounds which form another component of the catalyst composite will include alkyl aluminum halides such as dimethyl aluminum chloride, diethyl aluminum chloride, dipropyl aluminum chloride, dimethyl aluminum bromide, diethyl aluminum bromide, diproyl aluminum bromide, dimethyl aluminum iodide, diethyl aluminum iodide, dipropyl aluminum iodide, etc.

The porous support upon which the iron group metal compound is impregnated will include inorganic metal oxides such as alumina, silica, mixtures of oxides such as alumina-silica, alumina-zirconia-magnesia, etc. or crystalline aluminosilicates which are commonly known as zeolites.

If so desired the porous support of the type hereinbefore set forth may also have impregnated thereon a compound containing a metal of the group IVA of the Periodic Table. Examples of these compounds will comprise salts of these metals such as germanium chloride, germanium iodide, germanium fluoride, germanium sulfide, stannic bromide, stannic chloride, stannic oxychloride, stannic sulfate, lead acetate, lead perchlorate, etc. It is also contemplated within the scope of this invention that the metals of the iron group and group IVA may also be used in their elemental form as components of the catalytic composite.

Another component which may be present in the catalytic composite of the present invention will comprise an aluminum alkoxy compound which will act as an ativator for the catalytic composite. Examples of these aluminum alkoxy compounds will possess the generic formula $Al(OR)_3$ in which R comprises a lower molecular weight alkyl radical containing from one to about six carbon atoms. Some specific examples of these aluminum alkoxy compounds will include trimethoxy, aluminum, triethoxy aluminum, tripropoxy alumnium, triisopropoxy aluminum, tri-n-butoxy aluminum, tri-t-butoxy aluminum, tripentoxy aluminum, trihexoxy aluminum, etc. It is also contemplated with the scope of this invention that the catalytic compsite, may, if so desired, also contain an aluminum halide such as aluminum chloride, aluminum bromide, aluminum iodide, etc. It is to be understood that the aforementioned list of iron group metal compounds, Group IVA metal compounds, alkyl aluminum compounds, and aluminum alkoxy compounds, are only representative of the class of compounds which may be employed to form the catalytic composite of the present invention, and that said invention is not necessarily limited thereto.

The oligometrization catalyst which is used in the process of the present invention which may also be characterized by the method used to prepare the catalyst may be prepared in such a manner so as to provide the finished catalyst with the desired characteristics with regard to the selectivity of olefins obtained by the reaction of an olefinic hydrocarbon in the presence of such catalysts, as well as specificity of the product so obtained. The catalyst composite may be prepared by impregnating a porous support of the type hereinbefore set forth with a simple divalent iron group metal salt such as, for example, nickel nitrate, and a Group IVA metal salt such as tin chloride, preferably from an aqueous solution. Alternatively, the porous support may be impregnated with an aqueous iron group metal salt and the Group IVA metal may be incorporated into the support by any techniques which are well known to those skilled in the art. For example, sols such as tin or germanium sols may be prepared and impregnated into the support by well-known sol/gel techniques. In any event, after impregnation of the porous suport such as alumina, said impregnation being effected at ambient temperature and atmospheric pressure, the impregnated support is then subjected to a thermal treatment. By varying the temperature of the thermal treatment, it is possible to obtain a catalyst composite which will provide a greater selectivity to dimer products resulting from the oligomerization of the olefin which will be found to be present in greater amounts in contrast to trimer and tetramer products than are obtained when using other conventional oligomerization catalysts. The thermal treatment of the impregnated support is preferably effected in a range of from about 300° C. to about 450° C., the preferred thermal treatment temperature being in a range of from about 340° C. to about 360° C. The thermal treatment or calcination of the catalyst base containing the impregnated Group IVA metal or salt thereof and iron group metal salt in hydrate form will result in a weight loss due to a loss of water of hydration from the metal salt and will result in the formation of a non-stoichiometric hydrogen and oxygen-containing iron group metal compound which may also be referred to as a hydrate of an iron group metal salt. In the preferred embodiment of the invention, the mole ratio of water of hydration to iron group metal following the thermal treatment will be greater than 0.5:1 and preferably in a range of from about 0.5:1 to about 6:1. The thermal treatment of the catalyst base containing the iron group metal compound in the form of a hydrate will usually be effected for a period of time which is less than that required to completely drive off all of the water of hydration.

The thermal treatment or calcination of the catalyst base and the iron group metal salt at temperatures within the range hereinbefore set forth will result in a bonding of the iron group metal to the catalyst base usually by means of a metal-oxygen-base bond, the oxygen portion of the bond being supplied in part by the hydroxyl groups which are present on the surface of the porous support of the type hereinbefore set forth in greater detail.

Following the thermal treatment, the iron group metal impregnated catalyst base is then treated with an alkyl aluminum compound and an aluminum halide or aluminum aloxy compound to produce a catalyst of maximum activity. The treatment of the base with the aluminum alkyl compound and the aluminum halide or aluminum alkoxy compound is also effected at ambient temperture and atmospheric pressure utilizing a solution of the two compounds dissolved in an organic solvent such as benzene, toluene, isomeric xylenes, pentane, hexane, etc.

The addition of the organic solution, or conversely the addition of the impregnated base to the organic solution, will result in an exothermic reaction and, after thorough admixture, the resulting solution containing the impregnated base is allowed to return to room temperature. The solvent may then be removed by conventional means such as decantation, evaporation, filtration, etc. and the catalyst composite may then be washed with an organic solvent to remove residue or trace portions of unwanted compounds. Thereafter, the catalyst may then be dried by purging with nitrogen, and recovered. In the finished composite, the mole ratio of alkyl aluminum compound to iron group metal is from about 0.05:1 to about 6:1, preferably in a range of from about 0.1:1. The iron group metal is present in said composite, on an elemental basis, in an amount in the range of from about 1% to about 20% by weight of the composite, and preferably in an amount in a range of from about 1% to about 10%. In addition, Group IVA metal will also be present in said composite, on an elemental basis, in an amount in the range of from about 0.1% to about 20% by weight of the composite, and preferably in an amount in the range of from about 1% to about 10%.

As will hereinafter be shown in greater detail, by preparing a catalyst which possesses the various components in the finished composite in mole ratios or weight percents within the ranges hereinbefore set forth, it is possible to selectively oligomerize often compunds containing from about 2 to about 6 carbon atoms with a concurrent obtention of desirable isomers in each of the oligomer products. In addition, by utilizing the presence of a metal of the Gropu IVA of the Periodic Table in the catalyst composite, as well as an aluminum alkoxide compound, it is possible to obtain a catalyst composite which will be more stable, in that it will not deactivate in the presence of the type of impurities hereinbefore set forth in greater detail which may themselves be present in the feedstock, and which may impede or deter the oligomerization reaction of the present invention.

As an example of how the catalyst composite which is used in the process of the present invention may be prepared, a predetermined amount of a porous base such as alumina, silica, silica-alumina, aluminosilicate, etc. which may be in the form of spheres, pellets, rods, etc. may be prepared in an appropriate apparatus such as an evaporator along with an aqueous solution of a hydrate of an iron group metal salt and a Group IVA metal salt. The mixture may be thoroughly admixed and following this, the apparatus heated to form the desired iron group metal and Group IVA metal impregnated base. The impregnated base may then be placed in a heating apparatus such as a tube furnace and treated with air while bringing the catalyst to a temperature of about 250° C. The heating is accomplished at a relatively slow rate and after the determined temperature has been reached, it is maintained thereat for an additional period of time which may range from about 2 to about 4 hours or more in duration. The calcination of the catalyst base is then effected by increasing the temperature to a predetermined level and maintaining thereat for a period of time sufficient to bring the mole ratio of water of hydration present in the iron group metal salt to a determined level which is preferably in an excess of about 0.5:1 moles of water of hydration per mole of iron group metal.

After allowing the calcination to proceed for this predetermined period of time, heating is discontinued and the catalyst base which contains from about 1% to about 20% by weight of iron group metal and from about 0.1% to about 20% by weight of Group IVA metal, is allowed to cool. The cooled base may then be admixed with a solution of an alkyl aluminum compound and an aluminum halide or aluminum alkoxy compound dissolved in an organic solvent. As previously discussed, the resulting reaction is exothermic in nature and after allowing the heat to dissipate, the resulting admixture is thoroughly stirred and allows to stand for a period of time which may range from about 1 to about 100 hours or more in duration. At the end of this period, the organic solvent is removed by decantation, filtration, centrifugation, etc. and the solid catalyst is washed to remove any unreacted material. After washing, the catalyst is then dried in an inert atmosphere such as that provided for by the presence of nitrogen, and recovered.

The process of the present invention in which olefinic hydrocarbons are oligomerized in the presence of hydrogen by contacting the olefins with a catalyst of the type previously described is effected at oligomerization conditions which will inlcude a temperature in the range of from about $-20°$ C. to about 200° C., the preferred range being from about 30° C. to about 100° C. and a pressure in the range of from about 2413 kPa (350 psig) to about 6895 kPa (1,000 psig). The pressure which is utilized to effect the reaction may be the autogenous pressure provided for by the feedstock, if in gaseous phase, or, the feedstock may supply only a partial pressure, the remainder of said pressure being provided for by the hydrogen and/or an inert gas such as nitrogen, helium, argon, etc. If the olefinic feedstock is liquid in nature, the pressure may then be afforded in like manner by the hydrogen as the full pressure or a partial pressure. In the latter case, the remainder of the pressure may again be provided by introduction of an inert gas of a similar type into the reaction zone. The amount of hydrogen which is employed in the present process will be in a range of from about 0.01 to about 1.0 mole percent based upon the olefinic hydrocarbon feed, the present range being from about 0.01 to about 0.7 mole percent. It is contemplated within the scope of this invention that an excess of hydrogen may be present in the feedstream without having a deleterious effect upon the reaction. In addition, the olefinic hydrocarbon feed is also blended with from about 0.1% to about 80% of the paraffinic hydrocarbon counterpart of the particular olefin. For example, if propylene is to undergo oligomerization, the paraffinic hydrocarbon will comprise propane; likewise, if a butene is to undergo oligomerization the paraffinic portion of the feedstream will comprise butane. As was previously discussed, the presence of hydrogen in the feedstream will provide a stability to the catalytic composite, especially when the olefinic feedstream contains impurities, and especially sulfur impurities. Olefinic hydrocarbons which may be subjected to the oligomerization process of the present invention may contain from 2 to about 8 carbon atoms, such olefinic hydrocarbons including ethylene, propylene, butene-1, pentene-2, as well as the isomeric pentenes, hexens, heptenes, and octenes.

It is contemplated within the scope of this invention that the oligomerization process may be effected in either a batch or continuous type operation. For example, when a batch type operation is employed, a quantity of the novel catalyst composite of the present invention may be placed in an appropriate apparatus such as, for example, an autoclave of the rotating, mixing or stirring type. If the olefinic feedstock is in gaseous form, the desired amount of hydrogen is admixed with the olefinic feedstock or mixture of olefinic and paraffinic hydrocarbon of similar carbon length and the resulting admixture is charged to the sealed autoclave until the desired operating pressure has been attained. The apparatus is then heated to the desired operating temperature and maintained thereat for a predetermined period of time which may range from about 1 to about 6 hours or more in duration. At the end of this period of time, heating is discontinued and after the apparatus and contents thereof have returned to room temperature, the excess pressure is discharged and the autoclave is opened. The reaction product is recovered, separated from the catalyst by conventional means such as decantation, filtration, centrifugation, etc. and, if so desired, subjected to fractional distillation whereby the various isomers may be separated, one from another, and stored. Conversely, if so desired, the reaction product comprising a mixture of isomers may be recovered and stored per se without separating the various isomeric fractions which are present in the product mixture.

In the event that the olefinic charge stock is liquid form, the hydrogen in a predetermined amount is them charged to the feedstock and the resulting mixture again charged to the reactor which is in sealed condition. If the amount of hydrogen present in the feedstock is not sufficient to afford the desired operating pressure, the remainder of the operating pressure is afford by the introduction of an inert gas of the type hereinafter set forth. The remainder of the operating procedure to obtain the desired oligomer product is then carried out in a manner similar to that previously described.

When utilizing a continuous method of operation to obtain the desired oligomer products, a quantity of the catalyst composite is placed in an appropriate apparatus. The feedstock comprising the olefinic hydrocarbon, after admixture with hydrogen, is continuously charged to this reactor which is maintained at the proper operating conditions of temperature and pressure. As in the case of the batch-type operation, the desired operating pressure may be provided for by the olefinic hydrocarbon and hydrogen admixture or by the addition of a heated inert gas. After passage through the reactor for a predetermined period of time, the reactor elluent is continuously discharged and the reaction product may be recovered and passed to storage or it may be passed to a distillation apparatus whereby separation of the various isomers and oligomers may be effected. Any unreacted olefinic hydrocarbon which is recovered from the reactor effluent may be recycled back to the reactor to form a portion of the feed charge.

Inasmuch as the catalyst composite of the present invention is in solid form, the continuous method of opearation for obtaining the desired oligomers of the olefinic hydrocarbons may be effected in various types of operations. For example, in one type of operation, the catalyst is positioned as a fixed bed in the reaction zone and the olefinic feedstock is charged so that it passes over the catalyst bed in either an upward or downward flow. Another type of continuous operation which may be employed comprises the moving bed type of operation in which the catalyst bed and the feedstock are passed through the reaction one either concurrently or countercurrently to each other. In addition to the fixed or moving bed type of operation, it is also contemplated that the slurry type of operation may be employed, especially when the olefinic hydrocarbon feedstock is in liquid form. When this type of operation is employed, the catalyst is charged to the reactor as a slurry in the olefinic feedstock.

It is also contemplated within the scope of this invention that the presence of hydrogen in the reaction zone may also be afforded by intermittently charging predetermined amounts of hydrogen into the zone during the reaction period in order to maintain the necessary amount of hydrogen in the reaction zone to avoid poisoning the catalytic composite.

Examples of oligomers of olefinic hydrocarbons which may be obtained when effecting the process of the present invention whereby said olefin is oligomerized in the presence of hydrogen and the desired catalyst composite will include n-butene, isobutene, n-hexene, methyl pentene, dimethyl butene, n-octene, the isomeric methyl heptenes, dimethyl hexenes, n-dodecene, the isomeric methyl undecenes, dimethyl decenes, etc. By controlling the operating conditions of temperature and pressure, it is possible to obtain particularly desirable oligomer products which may comprise either dimers or trimers of the olefinic monomer. Thus, the catalyst composite and the presence of a hydrogen will combine to afford products which find particular uses for the finished product.

The following examples are given for purposes of illustrating the process of the present invention as well as preparation of the catalyst composites which are utilized to effect said process. However, it is to be understood that these examples are merely illustrative in nature and that the present invention is not necessarily limited thereto.

EXAMPLE I

A catalyst for use in the process of the present invention was prepared by impregnating 126.8 g of spherical alumina with an aqueous solution of 33.65 g of nickel nitrate hexahydrate, 3.48 g of concentrated nitric acid and 250 cc of water. The impregnation was effected in a steam-jacketed rotary evaporation at room temperature and atmospheric pressure. The mixture was rotated at room temperature for a period of 0.5 hours, following which steam was introduced into the jacket of the evaporator. After a period of 4 hours of rotation, the aqueous impregnation liquors had evaporated and the impregnated alumina containing 5.56 weight percent nickel was recovered. The impregnated base was loaded into a tube furnace and a flow of air was established in which the air passed through the catalyst bed at a rate of 600 cc/min. The catalyst was brought to a temperature of 250° C., maintained thereat for a period of 3 hours, following which the temperature was increased to 400° C. and maintained thereat for an additional period of 2 hours. Following this, heating was discontinued and the impregnated catalyst base was recovered.

After cooling, the impregnated alumina was then placed in a glove box under a nitrogen atmosphere. Activation of the catalyst was accomplished by adding 1.56 g of aluminum chloride and 7.21 g. of diethyl aluminum chloride per 100 cc of support. The activating compounds were added to the glove box in a hexane/-toluene solvent. The addition of the activator was accomplished by slowly adding the solution over a period of 20 minutes to the catalyst base inasmuch as the reaction was exothermic in nature and it was desired to control the heat of the reaction. After completion of the addition, the catalyst composite was allowed to stand for a period of 16 hours and thereafter the solvents were decanted. The catalyst composite was then washed with 6 portions of isopentane utilizing from 100 to 150 cc per wash. The resulting catalyst composite was then allowed to dry by evaporation of the excess isopentane while maintaining an atmosphere of nitrogen in the glove box.

EXAMPLE II

In this example, a second catalyst composite was prepared by impregnating 126.8 g of 0.32 cm (⅛ inch) alumina spheres with an aqueous solution of nickel nitrate and stannic chloride pentahydrate. The impregnating solution was prepared by admixing 33.65 g of nickel nitrate hexahydrates, 11.85 g of stannic chloride pentahydrate with 3.48 g of concentrated nitric acid in 250 cc of water. The impregnation of the base with the aqueous solution was accomplished in a manner similar to that set forth in Example I above. After rotation of the evaporator in the presence of steam for a period of 4 hours, the impregnating liquors had evaporated and the spherical alumina impregnated with nickel and tin was poured from the evaporator. The catalyst composite was placed in a tube furnace under a flow of air and calcined at a temperature of 250° C. for a period of 3 hours, followed by calcination at 400° C. for an additional period of 2 hours.

Activation of the catalyst base was effected by passing said base covered with a hexane/toluene solution in an Erlenmeyer flask into a glove box followed by addition of a hexane/toluene solution containing 1.56 g of aluminum trichloride and 7.25 g of diethyl aluminum chloride per 100 cc of support. The addition of the activating solution took place over a period of 20 minutes to prevent overheating of the catalyst base due to evolvement of heat resulting from the exothermic nature of the reaction. Upon completion of the addition, the mixture was allowed to stand for a period of 16 hours and the hexane/toluene solution was decanted. The catalyst composite was then washed with 6 portions of isopentane and allowed to dry in a glove box in a nitrogen atmosphere.

EXAMPLE III

The catalyst which was prepared in accordance with Example II above was utilized in the oligomerization of a butene feed. The feed comprised a mixture of 71.2 weight percent of n-butene and 28.8 weight percent n-butane to which was added 27 weight ppm of sulfur in the form of dimethyldisulfide. The oligomerization was effected by placing 50 cc of the catalyst in a tubular reactor having a 1.27 cm (0.5 inch) inner diameter. The feedstock was charged downflow to the reactor at an LHSV of 20 hr$^{-1}$ for a period of 12 hours. In the series of tests labeled A (Table 1 below), the feed charger was pressured to 1379 kPa (200 psig) with nitrogen while test B was performed by pressuring the feed charger to 1379 kPa (200 psig) with hydrogen. The amount of hydrogen added to the feed was about 0.1 mole percent Various catalyst bed inlet temperatures were used; this and the activity of the catalyst system determined what the catalyst bed maximum temperature would be. Oligomerization is highly exothermic so the catalyst bed maximum temperatures were greater than the inlet temperatures. Hydrogen activates in catalyst so, for a given inlet temperature, the catalyst bed maximum temperature was always greater when hydrogen was present. For both the A and B tests, we measured the rates at which the catalyst bed maximum temperature moved down the bed. The dimethyl disulfide induced deactivation occurs much as chromatography, that is, the dimethyl disulfide first deactivates the topmost part of the catalyst bed, then lower parts. The rate of movement of catalyst bed maximum temperature is thus a measure of the rate of deactivation. We tested the rates of movement in Table 1 as ΔMax/ΔTime (inches per hour). The lowest rates of movement correspond to slower deactivation.

TABLE 1

| Catalyst I | | |
|---|---|---|
| Catalyst Bed Maximum | ΔMax/ΔTime | |
| Temperature (0° C.) | A | B |
| 40 | 0.21 | |
| 50 | | 0.17 |
| 64 | | 0.16 |
| 82 | 0.19 | 0.14 |
| 107 | 0.185 | |

EXAMPLE IV

In this example, a catalyst which was prepared in accordance with Example II above was utilized in the oligomerization of butene utilizing similar feeds and similar conditions to those set forth in Example III above. Again run A was performed in the presence of nitrogen in the feedstock while run B utilized hydrogen in the feedstock. The results of these two runs are set forth in Table 2 below.

TABLE 2

| Catalyst II | | |
|---|---|---|
| Catalyst Bed Maximum Temperature (0° C.) | ΔMax/ΔTime A | B |
| 42 | 0.155 | |
| 48 | | 0.125 |
| 66 | 0.125 | |
| 70 | | 0.085 |
| 76 | 0.11 | 0.085 |
| 78 | | 0.08 |
| 88 | 0.105 | |
| 90 | | 0.07 |

It is noted from a comparison of runs A and B in Tables 1 and 2 that the presence of hydrogen in the feedstock stabilized both catalysts during the oligomerization of the butene feed containing sulfur as an impurity.

EXAMPLE V

The products resulting from the oligomerization reaction hereinbefore described were analyzed by gas chromatographic methods. The first analysis which pertained to the initial conversion of the n-butene with respect to the maximum temperature of the catalyst bed was made on both runs A, which were in the presence of nitrogen and runs B, which were in the presence of hydrogen. The results of this analysis are set forth in the tables below. Table 3 shows the results obtained when using the catalyst prepared according to Example I and Table 4 shows the results obtained when using the catalyst prepared according to Example II.

TABLE 3

| Catalyst I | | |
|---|---|---|
| Catalyst Bed Maximum Temperature (0° C.) | Initial n-Butene Conversion (wt. %) A | B |
| 40 | 85 | |
| 50 | | 94 |
| 60 | 83 | |
| 66 | 82 | |
| 68 | | 92 |
| 83 | 76 | |
| 107 | 72 | |

TABLE 4

| Catalyst II | | |
|---|---|---|
| Catalyst Bed Maximum Temperature (0° C.) | Initial n-Butene Conversion (wt. %) A | B |
| 42 | 88 | |
| 46 | | 96 |
| 50 | | 95 |
| 62 | 88 | |
| 66 | 86 | |
| 68 | | 92 |
| 70 | | 96 |
| 76 | 85 | 92 |
| 82 | | 94 |
| 88 | 75 | |
| 90 | | 88 |

It is to be noted from the above tables that the initial conversion of butene was greater at all maximum catalyst bed temperatures when the oligomerization reaction was effected in the presence of hydrogen. In addition, initial selectivity analyses disclose that there was no distinction in selectivity of $C_8^=+$ or $C_8^=$ when effecting the reaction in the presence of nitrogen or hydrogen.

Further analyses of the products when using a catalyst prepared according to Example II with respect to $C_8^=$ and $C_8^=+$ selectivities as a function of the butene conversion are set forth in Table 5 below.

TABLE 5

| Catalyst II | | |
|---|---|---|
| n-Butene Conversion Wt. % | Selectivity Wt. % A | B |
| $C_8^=$ | | |
| 75 | 82 | |
| 84 | 81 | |
| 85 | 83 | |
| 86 | 80 | |
| 92 | | 75 |
| 94 | | 73 |
| $C_8^=+$ | | |
| 75 | 18 | |
| 84 | 19 | |
| 85 | 17 | |
| 86 | 20 | |
| 92 | | 25 |
| 94 | | 27 |

It is to be noted that the presence of hydrogen as exemplified by the figure set forth under column B resulted in a greater conversion of the product to $C_8^=+$ than when the reaction was effected in the absence of hydrogen as exemplified by the figure set forth in column A. The reaction is sensitive to hydrogen in the production of trimers in a way which is contrary to the teachings of prior references. These references taught that hydrogen may be present in the reaction to control the molecular weight of the product obtained during the polymerization or oligomerization reaction, said control of molecular weight usually resulting in the production of lower molecular weight products.

We claim as our invention:

1. A process for the oligomerization of an olefinic hydrocarbon which comprises passing a feedstream of said olefinic hydrocarbon into an oligomerization zone, contacting said oelfinic hydrocarbon in said oligomerization zone with catalyst composite, which has been prepared by the process of impregnating a porous support with an aqueous solution containing an iron group metal salt, calcining said impregnated, support at a temperature in the range of from about 300° C. to about 450° C. and contacting said impregnated calcined support with a solution of an alkyl aluminum compound, at oligomerization conditions in the presence of hydrogen to form an oligomer of said olefinic hydrocarbon, and recovering said oligomer.

2. The process as set forth in claim 1 further characterized in that said porous support is further impregnated with an aqueous solution of Group IVA metal salt.

3. The process as set forth in claim 1 further characterized in that said impregnated calcined support is contacted with a solution of an aluminum alkoxy compound.

4. The process as set forth in claim 1 further characterized in that said composite further contains an aluminum halide.

5. The process as set forth in claim 1 in which said oligomerization conditions include a temperature in the range of from about −20° to about 200° C. and a pressure in the range of from about 2,413 kPa (350 psig) to about 6,895 kPa (1,000 psig).

6. The process as set forth in claim 1 in which said hydrogen is admixed with said olefinic hydrocarbon feedstream prior to entry into said oligomerization zone.

7. The process as set forth in claim 1 in which said hydrogen is present in said olefinic hydrocarbon feedstream in an amount in the range of from about 0.01 to about 1.0 mole percent hydrogen.

8. The process as set forth in claim 1 in which said olefinic hydrocarbon contains from 2 to about 8 carbon atoms.

9. The process as set forth in claim 1 in which said iron group metal is present in said catalytic composite, on an elemental basis, in an amount in the range of from about 1% to about 20% by weight of said composite.

10. The process as set forth in claim 2 in which the weight ratio of said Group IVA metal to said iron group metal is in a range of from about 0.1:1 to about 10:1.

11. The process as set forth in claim 1 in which said alkyl aluminum compound is present in said composite in a mol ratio to said iron group metal in a range of from about 0.05:1 to about 6:1.

12. The process as set forth in claim 1 in which said iron group metal is nickel.

13. The process as set forth in claim 1 in which said iron group metal is iron.

14. The process as set forth in claim 2 in which said Group IVA metal is tin.

15. The process as set forth in claim 1 in which said Group IVA metal is germanium.

16. The process as set forth in claim 1 in which said alkyl aluminum compound is dimethylaluminum chloride.

17. The process as set forth in claim 1 in which said alkyl aluminum compound is diethylaluminum chloride.

18. The process as set forth in claim 3 in which said aluminum alkoxy compound is tri-t-butoxy aluminum.

19. The process as set forth in claim 3 in which said aluminum alkoxy compound is tri-sec-butoxy aluminum.

20. The process as set forth in claim 4 in which said aluminum halide is aluminum chloride.

21. The process as set forth in claim 1 in which said olefinic hydrocarbon comprises propylene and said oligomer is a mixture of hexene, methylpentene and dimethylbutene.

22. The process as set forth in claim 1 in which said olefinic hydrocarbon comprises butene and said oligomer is a mixture of octene, methylheptene and dimethylhexene.

* * * * *